(12) United States Patent
Zeijlemaker et al.

(10) Patent No.: US 7,623,930 B2
(45) Date of Patent: Nov. 24, 2009

(54) CONTROLLING TELEMETRY DURING MAGNETIC RESONANCE IMAGING

(75) Inventors: Volkert A. Zeijlemaker, Landgraaf (NL); Steven D. Goedeke, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 667 days.

(21) Appl. No.: 10/673,934

(22) Filed: Sep. 30, 2003

(65) Prior Publication Data

US 2005/0070975 A1    Mar. 31, 2005

(51) Int. Cl.
*A61N 1/08* (2006.01)
(52) U.S. Cl. .................................................. 607/60
(58) Field of Classification Search .............. 607/60, 607/1, 2, 31, 32, 9; 600/411, 413
See application file for complete search history.

(56) References Cited

U.S. PATENT DOCUMENTS

| 5,217,010 | A  | * | 6/1993 | Tsitlik et al. ................. 607/9 |
| 2003/0167078 | A1 | * | 9/2003 | Weisner et al. ............. 607/60 |
| 2004/0073124 | A1 | * | 4/2004 | Axel ............................ 600/509 |

FOREIGN PATENT DOCUMENTS

WO    03/063962    8/2003

OTHER PUBLICATIONS

Definition for telemetry, www.answers.com, acessed Jun. 5, 2007.*
PCT International Search Report, PCT/US2004/031099, 5 pages.
William Pavlicek, et al., "The Effects of Nuclear Magnetic Resonance on Patients with Cardiac Pacemakers", *PACE*, vol. 18, Aug. 1995, pp. 1549-1555.
Jay A. Erlebacher, MD, et al., "Effect of Magnetic Resonance Imaging on DDD Pacemakers" *The American Journal of Cardiology*, vol. 57, Feb. 15, 1986, pp. 437-440.
Paresh M. Shah, MD, et al., "Life After Pacemaker Implantations: Management of Common Problems and Environmental Interactions",*Cardiology in Review*, vol. 9, No. 4, , 2001, pp. 193-201.
Gerhard Lauck et al., "Effects of Nuclear Magnetic Resonance Imaging on Cardiac Pacemakers", PACE, vol. 18, Aug. 1995, pp. 1549-1555.

* cited by examiner

*Primary Examiner*—George R Evanisko
*Assistant Examiner*—Alyssa M Alter
(74) *Attorney, Agent, or Firm*—Carol F. Barry; Michael J. Ostrom

(57) ABSTRACT

The invention is directed techniques for coordinating telemetry of medical devices with magnetic resonance imaging (MRI) techniques. By coordinating telemetry of a medical device with the performance of MRI techniques with, the use of telemetry during MRI may be facilitated. In one example, information indicative of electromagnetic radiation bursts in MRI techniques can be communicated to the medical device prior to execution. In another example, the medical device may identify the electromagnetic radiation bursts, e.g., by measuring for the presence of such bursts. In either case, the medical device can adjust its telemetry to improve communication during MRI.

23 Claims, 6 Drawing Sheets

CONTROLLING TELEMETRY DURING MAGNETIC RESONANCE IMAGING

FIELD OF THE INVENTION

The invention relates to magnetic resonance imaging (MRI) techniques.

BACKGROUND OF THE INVENTION

Magnetic resonance imaging (MRI) techniques make use of electromagnetic fields to create images of a patient. MRI techniques permit the generation of high-quality two- or three-dimensional images of a patient's body, which can then be examined by a physician for diagnosis purposes. In particular, MRI techniques permit the generation of internal images of a patient's flesh, blood, bones, cartilage, blood vessels, organs, and the like. The generated images can then be examined by physicians in order to diagnose disease, disorders or injuries and facilitate patient care.

MRI devices typically subject a patient to a very strong static magnetic field and a pulsed gradient magnetic field, and then apply pulses or bursts of electromagnetic radiation (typically radio frequency (RF) radiation bursts) to an area of the patient to be imaged. The strong magnetic field generally orients the protons of the patient's tissue in particular directions. However, the RF radiation bursts cause some of the patient's protons to resonate, or spin, at a particular frequency depending on the local magnetic field during application of the radiation burst. The resonance frequency in MRI is referred to as the Larmour frequency, which has a relationship with the local magnetic field. When the RF radiation burst is terminated, the resonating protons reorient themselves in accordance with the strong magnetic field of the MRI device, giving off energy in the process. The MRI device can detect the energy given off by the reorienting protons in order to create a high quality image of the patient's tissue.

A wide variety of medical devices have also been developed in order to monitor patient conditions or possibly deliver therapy to the patient. In many cases, the medical devices are implantable medical devices (IMDs) that are surgically implanted inside a patient for short or long term therapy. One common example of an IMD is a pacemaker. A pacemaker typically includes one or more pacing and sensing leads for delivery of pacing pulses to a patient's heart. Another example of an IMD is a combination pacemaker-cardioverter-defibrillator. Other examples include implantable brain stimulators, implantable gastric system stimulators, implantable nerve stimulators or muscle stimulators, implantable lower colon stimulators, implantable drug or beneficial agent dispensers or pumps, implantable cardiac signal loops or other types of recorders or monitors, implantable gene therapy delivery devices, implantable incontinence prevention or monitoring devices, implantable insulin pumps or monitoring devices, and so on.

Many implantable medical devices (IMDs) support telemetry. Telemetry generally refers to communication of data, instructions, and the like between a medical device and a medical device programmer. For example, the programmer may use telemetry to program a medical device to deliver a particular therapy to a patient. In addition, the programmer may use telemetry to interrogate the medical device. In particular, the programmer may obtain diagnostic data, event marker data, activity data and other data collected or identified by the medical device. The data may be used to program the medical device for delivery of new or modified therapies. In this manner, telemetry between a medical device and a programmer can be used to improve or enhance medical device therapy.

Telemetry typically involves wireless data transfer between a medical device and the programmer using radio frequency (RF) signals, infrared (IR) frequency signals, or other electromagnetic signals. Any of a variety of modulation techniques may be used to modulate data on a respective electromagnetic carrier wave. Alternatively, telemetry may be performed using wired connections, sound waves, or even the patient's flesh as the transmission medium. A number of different telemetry systems and techniques have been developed in order to facilitate the transfer of data between a medical device and the associated programmer.

BRIEF SUMMARY OF THE INVENTION

In general, the invention is directed to techniques for coordinating telemetry of medical devices with magnetic resonance imaging (MRI) techniques. Telemetry can disrupted if the medical device performing the telemetry is in close proximity to an MRI device during application of the electromagnetic radiation bursts or possibly the gradient magnetic fields. Specifically, the electromagnetic radiation bursts associated with MRI can make it difficult or impossible for a medical device to send or receive telemetric communications. By coordinating the performance of MRI techniques with telemetry of a medical device, the use of telemetry during MRI may be facilitated.

In one example, information indicative of electromagnetic radiation bursts (or possibly gradient fields) in MRI techniques can be communicated to the medical device prior to execution. The medical device can adjust telemetry according to the received information. For example, the information may define timing of the electromagnetic radiation bursts, such as a start time of one or more bursts, durations of the burst(s), time intervals between bursts, or the like. The medical device may use this information to disable or blank telemetry during the bursts, or the adjust the telemetry such that effective communication can more effectively occur between bursts, or possibly during the bursts.

In one embodiment, the invention provides a method of coordinating a medical device with MRI. The method may include identifying information associated with one or more MRI electromagnetic radiation bursts, and adjusting telemetry of a medical device during the electromagnetic radiation bursts based on the information.

In another embodiment, a method may include identifying an occurrence of one or more MRI electromagnetic radiation bursts, and adjusting telemetry of a medical device to allow for effective communication during the electromagnetic radiation bursts.

In another embodiment, the invention provides medical device such as an implantable medical device, a programmer, and MRI device, or any other implantable or non-implantable medical device. The device may include a telemetry unit to send communications to another device, and a control unit to adjust telemetry during MRI electromagnetic radiation bursts.

In another embodiment, the invention provides medical device comprising a telemetry unit send communications to another device, and a control unit to identify an occurrence of one or more MRI electromagnetic radiation bursts and adjust telemetry to allow effective communication during the electromagnetic radiation bursts.

In another embodiment, the invention provides a system comprising a first medial device and a second medical device.

Either of the first or second medical devices may comprise an implantable medical device, a programmer, and MRI device, or any other implantable or non-implantable medical device. In any event, the first medical device may transmit information indicative of one or more MRI electromagnetic radiation bursts, and the a second medical device may receive the information and adjust telemetry based on the information.

In another embodiment, the invention provides a system comprising a first medical device to apply MRI electromagnetic radiation bursts, and a second medical device to receive radiation from the electromagnetic radiation bursts and adjust telemetry during the electromagnetic radiation bursts.

In another embodiment, the invention provides an apparatus comprising means for sending communications to another device, and means for adjusting telemetry during MRI electromagnetic radiation bursts.

In another embodiment, the invention provides an apparatus comprising means for sending communications to another device, means for identifying one or more MRI electromagnetic radiation bursts, and means for adjusting telemetry to allow effective communication during the electromagnetic radiation bursts.

In an added embodiment, the invention provides a method of coordinating a medical device with MRI comprising performing MRI imaging techniques by applying a substantially constant strong magnetic field, applying one or more MRI electromagnetic radiation bursts, and imaging a patient following the MRI electromagnetic radiation bursts. The method may further include identifying information associated with one or more MRI electromagnetic radiation bursts, and adjusting telemetry of a medical device during the electromagnetic radiation bursts based on the information.

The different embodiments may be capable of providing a number of advantages. In general, by coordinating telemetry with MRI techniques, the use of telemetry during MRI can be facilitated. More specifically, by measuring or receiving information indicative of MRI electromagnetic radiation bursts (and possibly information indicative of the application of the gradient fields), a medical device can adjust its telemetry to allow for effective communication during the MRI procedure. The use of telemetry during the MRI procedure can allow for improved monitoring of the patient during the MRI. Moreover, telemetry during the MRI procedure may allow a physician to adjust medical device operation, e.g., via a programmer, if problems in the procedure warrant action by the medical device. In these ways and other ways, patient care may be enhanced by the invention.

The details of one or more embodiments of the invention are set forth in the accompanying drawings and the description below. Other features, objects, and advantages of the invention will be apparent from the description and drawings, and from the claims.

DETAILED DESCRIPTION OF THE INVENTION

The invention is directed to the coordination of telemetry of medical devices with magnetic resonance imaging (MRI) techniques. By adjusting telemetry during MRI, the use of telemetry during MRI may be facilitated. In one example, information indicative of electromagnetic radiation bursts in MRI techniques can be communicated to the medical device prior to application of the bursts. Also, information indicative of application of magnetic gradients may be communicated. The medical device can adjust telemetry according to the received information. In another example, the medical device may identify the electromagnetic radiation bursts, e.g., by measuring for the presence of such bursts. In either case, the medical device can adjust its telemetry to improve telemetric communication during MRI.

The medical device may adjust its telemetry in any of a number of different ways, upon identifying information associated with MRI electromagnetic radiation bursts (and possibly application of gradient fields). In one example, the medical device can blank or otherwise disable one or more telemetry components of the medical device specifically during the electromagnetic radiation bursts and/or application of gradient fields. In another example, the medical device can increase power of telemetry signals during the electromagnetic radiation bursts. In another example, the medical device can select a packet size for more effective communication between burst intervals. In these or other ways, a medical device may adjust its telemetry upon receiving information indicative of MRI electromagnetic radiation bursts, or upon measuring the presence of such radiation bursts.

Figure 1:
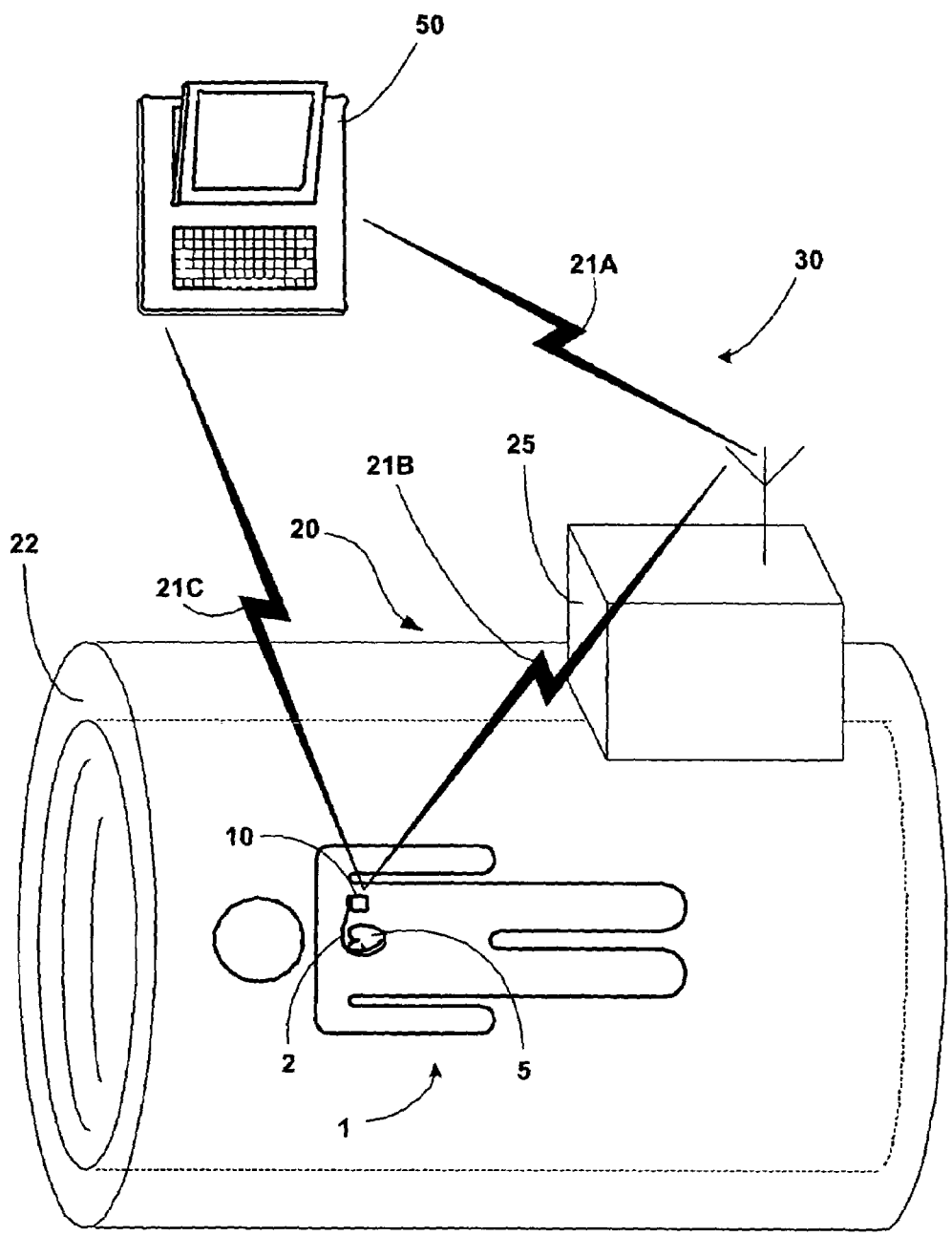
FIG. 1 is a conceptual diagram illustrating a magnetic resonance imaging (MRI) device, an implantable medical device (IMD), and a programmer communicating via telemetry.

FIG. 1 is a conceptual diagram of a system 30 including a magnetic resonance imaging (MRI) device 20, an implantable medical device (IMD) 10, and a programmer 50 communicating via telemetry. MRI device 20, IMD 10 and programmer 50 are all examples of medical devices, and will be referred to collectively as such. Programmer 50 and MRI device 20 communicate via telemetry signals 21A, MRI device 20 and IMD 10 communicate via telemetry signals 21B, and programmer 50 and IMD 10 communicate via telemetry signals 21C. In other embodiments, some of the respective connections may be wired connections, e.g., programmer 50 and MRI device 20 may have a wired connection instead of using telemetry. In any event, any or all of the telemetry between respective medical devices 10, 20 and 50 can be defined or adjusted specifically for compatibility with MRI techniques.

As conceptually illustrated in FIG. 1, patient 1 is located inside MRI device 20. Patient 1 has the IMD 10 surgically implanted in the patient's body. By way of example, IMD 10 is illustrated as a cardiac pacemaker that provides therapeutic stimulation to heart 5. However, in accordance with the invention, IMD 10 may generally comprise any of a wide variety of medical devices that can be implanted in the body of a human or other life form. Moreover, in some cases, the invention may be implemented with medical devices that are not implanted. By way of example, IMD 10 may take the form of an implantable cardioverter, an implantable defibrillator, or an implantable cardiac pacemaker-cardioverter-defibrillator. Other examples of IMDs that may benefit from the invention include implantable brain stimulators, implantable gastric system stimulators, implantable nerve stimulators or muscle stimulators, implantable lower colon stimulators, implantable drug or beneficial agent dispensers or pumps, implantable cardiac signal loops or other types of recorders or monitors, implantable gene therapy delivery devices, implantable incontinence prevention or monitoring devices, implantable insulin pumps or monitoring devices, and so forth.

Referring again to FIG. 1, IMD 10 may deliver pacing, cardioversion or defibrillation pulses to a patient via electrodes disposed on distal ends of one or more leads 2. In other words, one or more leads 2 may position one or more electrodes with respect to various cardiac locations so that IMD 10 can deliver pulses to the appropriate locations.

MRI device 20 may assume a wide variety of shapes, sizes or configurations. In the illustrated example, MRI device 20 defines a relatively large tubular cavity 22 into which patient 1 can be placed during performance of the MRI techniques. In other cases, however, MRI device 20 may define a much smaller cavity, e.g., for insertion of a patients arm, leg, head, or the like. MRI device 20 may assume a wide variety of shapes and sizes and may possibly allow access to a patient during the scan. In any case, MRI device 20 includes a set of MRI components, e.g., inside housing 25, such as circuitry, magnets, inductors and the like, that define operation of MRI device 20.

MRI device 20 makes use of electromagnetic fields to create images of patient 1. For example, MRI device 20 may subject a patient to very strong static magnetic fields and gradient fields via one or more permanent magnets or electromagnets located about cavity 22 or within housing 25. MRI device 20 then applies radiation bursts, e.g., pulses of electromagnetic radiation (typically radio frequency (RF) radiation) to an area of the patient 1 to be imaged. For example, housing 25 may house various components that generate and apply RF radiation bursts at desired frequencies associated with the particular tissue of patient 1 to be imaged.

The strong magnetic field generally orients the protons of patient 1 in particular directions by superimposing position dependent magnetic gradients. However, the RF radiation bursts cause some of the patient's protons to resonate, or spin, at a particular frequency during the application of the RF radiation bursts. The resonance frequency applied by MRI device 20 is referred to as the Larmour frequency, which has a linear relationship with the local magnetic field. When an RF radiation burst is terminated, the resonating protons reorient in accordance with the strong magnetic field of the MRI device, giving off energy in the process. MRI device 20 can detect the energy given off by the reorienting protons to create a high quality image of the tissue or matter of patient 1.

Programmer 50 communicates with IMD 10, MRI device 20, or both via telemetry. The illustration of programmer 50 is exemplary, and programmer 50 may alternatively assume any of a wide variety of shapes, sizes and configurations. In any case, programmer 50 may send wireless telemetry signals 21C to IMD 10 to program IMD 10 to deliver a particular therapy to a patient. In addition, programmer 10 may use telemetry to interrogate IMD 10, and request diagnostic data, event marker data, activity data and other data collected or identified by IMD 10. In that case, IMD 10 may send signals 21C to programmer 50 to transfer the requested data.

The transferred data may then be used by programmer 50 to program the IMD 10 for delivery of new or modified therapies. In this manner, telemetry between IMD 10 and a programmer 50 can be used to improve or enhance medical device therapy. Similarly, telemetry between programmer 50 and MRI device 20 can achieve similar advantages. Also, telemetry between MRI device 20 and IMD 10 may provide other advantages as described herein, such as the ability to communicate the information needed by IMD 10 to adjust its telemetry when such adjustments are needed for effective communication.

In accordance with the invention, the telemetry of one or more of medical devices 10, 20 and 50 is coordinated with the electromagnetic radiation bursts of MRI device 20, and possibly also coordinated with application of magnetic gradients. For example, medical devices 10, 20 and 50 adjust their telemetry during application of electromagnetic radiation bursts by MRI device 20. For IMD 10, the information indicative of such electromagnetic radiation bursts may be received by either MRI device 20 or programmer 50, or alternatively, may be measured or identified by IMD 10 upon application of the bursts by MRI device 20. In any case, once a given medical device 10, 20 or 50 obtains or measures the needed information defining the application of electromagnetic radiation bursts by MRI device 20, the given medical device can adjust its telemetry for effective communication during the MRI procedure. In the case where the medical device measures the occurrence of one or more electromagnetic radiation bursts, the telemetric adjustments may occur automatically in response to such detection.

In one example, upon identifying the timing of electromagnetic radiation bursts, a medical device can blank or otherwise disable and protect one or more telemetry components specifically during the bursts. In another example, upon identifying the timing of electromagnetic radiation bursts, the medical device can increase power of its telemetry signals during the bursts. In yet another example, upon identifying the timing of electromagnetic radiation bursts, the medical device may select or adjust a packet size in order to ensure that the packets can be communicated between successive burst intervals. In still other examples, the medical device may change communication modes during burst intervals, e.g., using sound waves rather than electromagnetic signals during the bursts. In these or other ways, a medical device may adjust its telemetry upon receiving information indicative of MRI electromagnetic radiation bursts, or upon measuring the presence of such electromagnetic radiation bursts.

Figure 2:
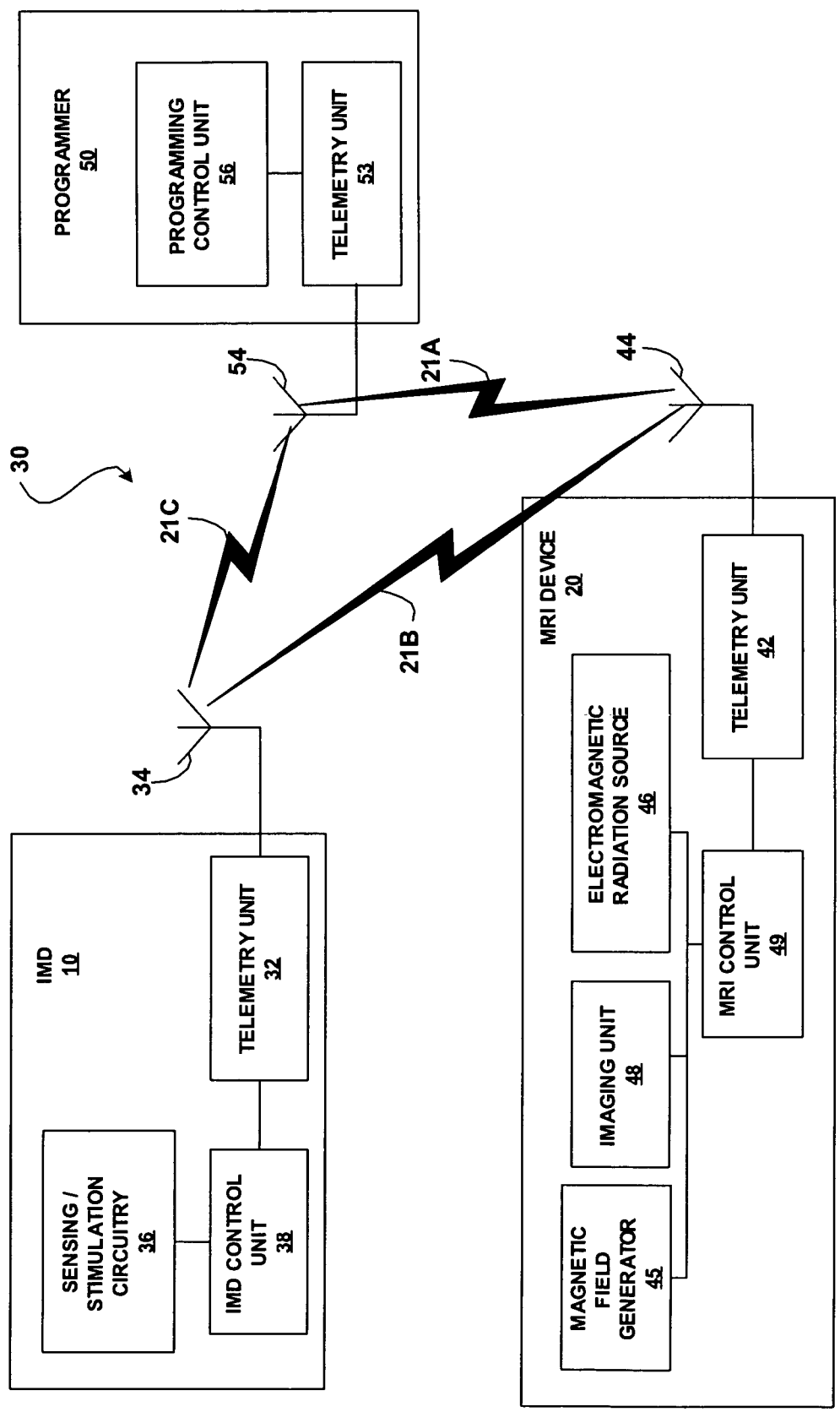
FIG. 2 is a functional block diagram of a MRI device, an IMD, and a programmer communicating via telemetry

FIG. 2 is a functional block diagram of system 30 that includes MRI device 20, IMD 10 and programmer 50. In system 30, programmer 50 and MRI device 20 communicate via telemetry signals 21A, MRI device 20 and IMD 10 communicate via telemetry signals 21B, and programmer 50 and IMD 10 communicate via telemetry signals 21C. In accordance with the invention, any or all of the telemetry between respective medical devices 10, 20 and 50 can be defined or adjusted specifically for compatibility with MRI techniques.

Any of a wide variety of telemetry techniques may be used to facilitate transfer of information between the respective medical devices 10, 20 and 50. In accordance with the invention, the transferred information may provide a given medical device with an indication of the timing, e.g., the start time and duration, of one or more electromagnetic radiation bursts to be applied by MRI device 20. Accordingly, the medical device that receives or otherwise determines this information relating to the electromagnetic radiation bursts can use the information to define adjustments to its telemetry as described herein. Information indicative of application of magnetic gradients may be used in a similar fashion, if desired.

IMD 10 includes a telemetry unit 32 and an antenna 34 which facilitate transmission and reception of wireless signals 21C and 21B to and from MRI device 20 and programmer 50. IMD 10 also includes circuitry 36 for sensing and/or stimulating a patient for therapeutic purposes. For example, sensing/stimulation circuitry 36 may include electrodes disposed on medical leads and implanted at locations in a patient where sensing and stimulation occurs. Sensing/stimulation circuitry 36 typically includes one or more amplifiers to enhance the sensed signals and to generate the electrical potentials needed for effective stimulation.

IMD control unit 38 coordinates circuitry 36 so that sensing and stimulation occurs at proper times. In particular, IMD control unit 38 may define various sensing and stimulation algorithms that define the therapy to be provided. For example, if IMD 10 is a cardiac pacemaker, IMD control unit 38 may execute algorithms that receive sensed information from circuitry 36 and determine whether an arrhythmia has occurred in the heart. If IMD control unit 38 identifies an arrhythmia, it may store this information, and possibly respond by causing circuitry 36 to provide stimulation therapy specifically for the identified arrhythmia. IMD control unit 38 may execute a number of algorithms to identify and respond to a wide variety of potential arrhythmias in the patient's heart.

MRI device 20 also includes a telemetry unit 42 and an antenna 44 to facilitate transmission and reception of wireless signals 21A and 21B to and from programmer 50 and IMD 10. In operation, MRI device 20 makes use of electromagnetic fields to create images of a patient. Such MRI techniques are particularly useful in creating images of blood flow, images to facilitate identification of tumors, soft tissue injuries and the like, or other images that can not be easily generated via conventional imaging techniques such as X-ray techniques, or the like.

MRI device 20 includes one or more magnetic field generators 45 and one or more electromagnetic radiation sources 46. In particular, magnetic field generator 45 generates a relatively large magnetic field, e.g., in the range of 0.2 to 20 Tesla. Magnetic field generator 45 may include a permanent magnet, an electromagnet, or the like, and may also include gradient field generators to impose gradient fields during the MRI. In addition, MRI device 20 includes one or more electromagnetic radiation sources 46, such as RF radiation sources. As outlined above, MRI device 20 subjects a patient to a very strong magnetic field via magnetic field generator 45. Electromagnetic radiation source 46 of MRI device 20 then applies pulses or bursts of electromagnetic radiation (typically bursts of radio frequency (RF) radiation) to an area of the patient to be imaged. The strong magnetic field of magnetic field generators 45 generally orients the protons of a patient in particular directions, but the RF radiation bursts by electromagnetic radiation source 46 causes some of the patient's protons to resonate with a frequency typical for the local magnetic fields. When the RF radiation burst is terminated, the resonating protons reorient in accordance with the strong magnetic field of the magnetic field generators 45, giving off energy in the process.

Imaging unit 48 of MRI device 20 receives and detects the energy given off by the reorienting protons. Imaging unit 48 uses the detected energy given off by the reorienting protons to create one or more images of the tissue or matter of the patient. In this manner, MRI device 20 is used to create medical images.

MRI control unit 49 coordinates the application of RF radiation bursts by electromagnetic radiation source 46, and the imaging by imaging unit 48. In particular, MRI control unit 49 may define the timing of the RF radiation bursts by electromagnetic radiation source 46, including the start time and duration of any given burst. MRI control unit 49 may perform one or more algorithms to coordinate and define the MRI techniques of MRI device 20. In addition, MRI control unit 49 may blank one or more electrical components of MRI device 20 during application of the RF radiation bursts, e.g., to avoid electrical interference or malfunction of the components.

In accordance with one embodiment of the invention, MRI device 20 communicates information to IMD 10 and/or programmer 50 via telemetry unit 42 and antenna 44. In some cases, antenna 44 may be an antenna mounted on programmer 50, and in other cases, antenna 44 may comprise at least a portion of a wand connected to programmer 50, which can be placed in close proximity to IMD. In any case, information in MRI control unit 49 defining the timing of RF radiation bursts to be applied by electromagnetic radiation source 46 can be communicated to IMD 10 and programmer 50 via telemetry unit 42 and antenna 44. This timing information may include a start time of a burst, a duration of a burst, information regarding sequence of bursts, or the like, that defines when one or more of the RF radiation bursts are to occur.

MRI control unit 49 may generate this information specifically for transmission to IMD 10 and programmer 50, or may have already generated the information for purposes of blanking one or more components of MRI device 20 during application of the RF radiation bursts. In the later case, the same information used by MRI control unit 49 to cause blanking of one or more components of MRI device 20 can be communicated to IMD 10 and programmer to facilitate telemetry adjustments consistent with the MRI. IMD 10 and/or programmer 50 may use the timing information to blank telemetry during the bursts, adjust signal strength of telemetry during the bursts, select packets sizes small enough for effective communication between bursts, or make other adjustments to the telemetry. In particular, the respective control unit or telemetry unit of the device making the adjustments can effectuate the adjustments. The information may be sent with sufficient lead time in order to ensure that adjustments to the telemetry can be made prior to commencement of the electromagnetic radiation bursts.

FIGS. 3-6 are flow diagrams illustrating techniques for coordinating telemetry of a medical device with MRI techniques according to embodiments of the invention. For simplicity, FIGS. 3-6 will be described from the perspective of IMD 10. It is understood, however, that the same or similar techniques could be applied by other medical devices, including any of the implantable medical devices listed above such as programmer 50, or in some cases, MRI device 20 that performs the MRI. Also, the same or similar techniques of FIGS. 3-6 may be used to communicate or identify information indicative of application of magnetic gradients in the MRI, if desired.

Figure 3:
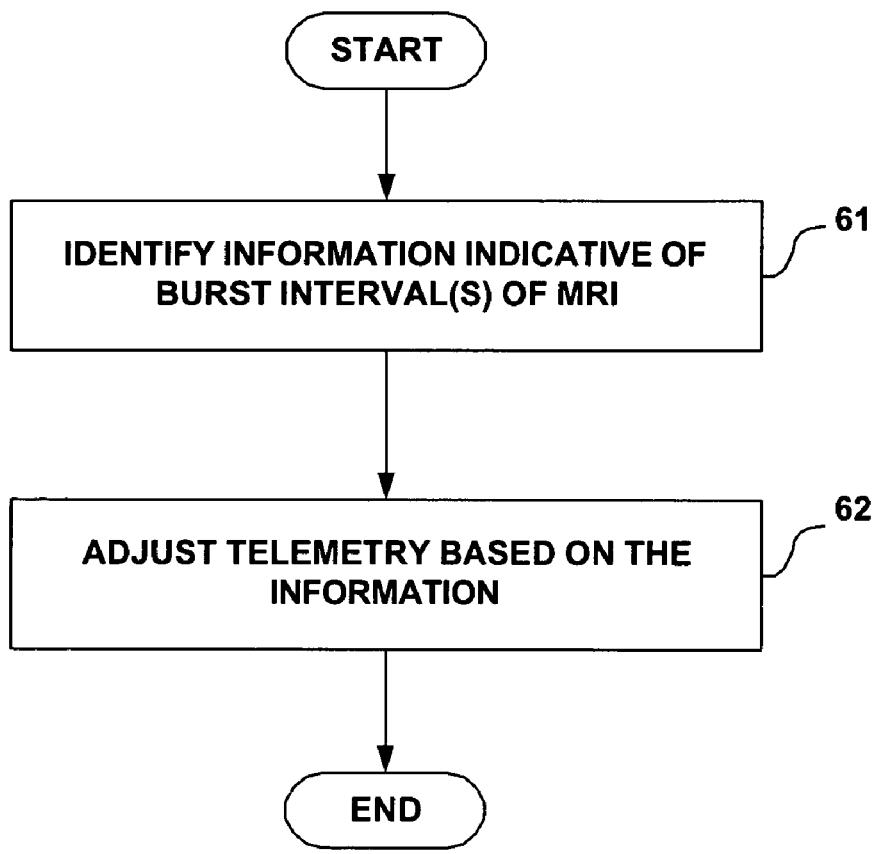
FIGS. 3-6 are flow diagrams illustrating techniques for coordinating medical device telemetry with MRI techniques according to embodiments of the invention.

As shown in FIG. 3, IMD 10 identifies information indicative of one or more burst intervals of MRI (61). For example, IMD 10 may receive a signal from MRI device 20 or programmer 50 indicating timing of one or more electromagnetic burst intervals. Alternatively, IMD 10 may receive radiation from one or more electromagnetic radiation bursts and measure or calculate characteristics of the bursts such as timing of one or more bursts, duration of one or more bursts, signal strength of one or more bursts, a timed sequence of the bursts, or the like, in order to obtain the information needed to adjust telemetry. In other words, IMD 10 may identify the occurrence of one or more bursts, and measure characteristics associated with the occurrence to define the information needed to adjust telemetry.

The timing of a burst interval may be defined, e.g., by a start time and a duration, although other variables may also be included in the timing such as a timing sequence that defines timing for a number of bursts, time intervals between successive bursts, strength of the bursts, and so on. In some cases, the information received or measured by IMD 10 can be used to synchronize an internal clock of IMD 10 with that of MRI device 20, e.g., to ensure that IMD 10 can properly identify the start time and end time of subsequent bursts. In any case, upon receiving the signal that indicates the timing of the burst interval(s), IMD 10 adjusts its telemetry (62) to allow for effective telemetric communication during the MRI.

Upon identifying the information relating to the electromagnetic bursts of MRI device 20 (61), IMD 10 may adjust its telemetry (62) in any of a number of different ways. In one example, IMD 10 blanks or disables one or more components or circuits of telemetry unit 42, specifically during the bursts. In another example, IMD 10 increases the power of its telemetry signals during the bursts. In yet another example, IMD 10 selects or adjusts a packet size of telemetry signals in order to ensure that the packets can be communicated between successive burst intervals. In still other cases, IMD 10 may select a different telemetry mode during burst intervals, or during the MRI procedure. In these or other ways, IMD 10 may adjust its telemetry upon receiving information indicative of MRI electromagnetic radiation bursts, or upon measuring the presence of such electromagnetic radiation bursts.

Figure 4:
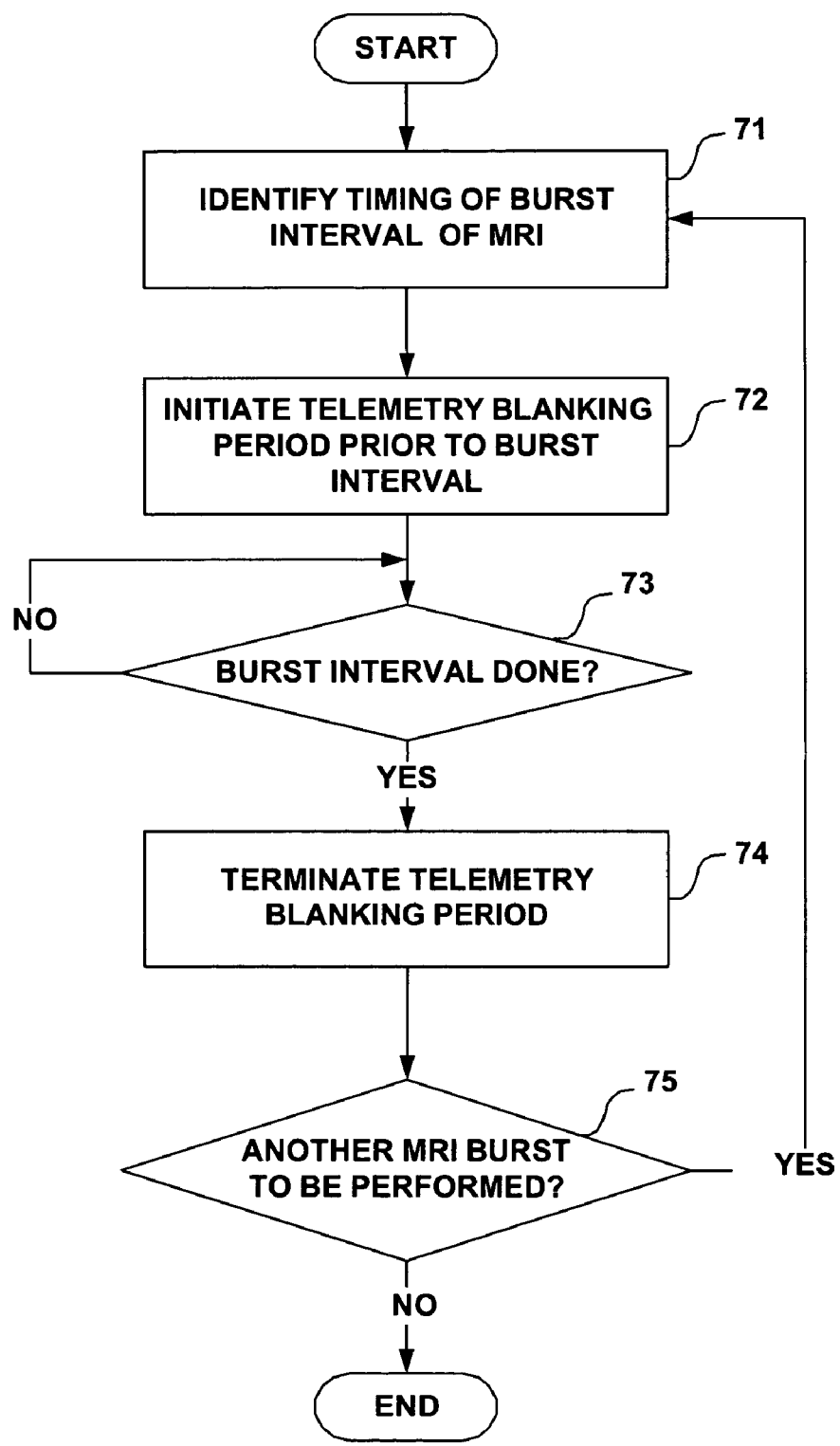

FIG. 4 is another flow diagram illustrating a technique for coordinating telemetry of a medical device with MRI techniques. As shown in FIG. 4, IMD 10 identifies timing of a burst interval of MRI (71). Again, IMD 10 may identify such timing by receiving a signal indicative of the timing from MRI device 20 or programmer 50, or by measuring the presence of an electromagnetic radiation burst and calculating the timing. In any case, upon identifying the timing of a burst interval IMD 10 initiates a blanking period for its telemetry just prior to the burst interval (72). For example, IMD control unit 38 may temporarily disable some or all of the circuitry of telemetry unit 32 during the blanking period. The blanking period may be defined to substantially correspond to the burst interval, or may be made slightly larger than the burst interval in order to ensure that telemetry blanking period does not begin late or terminate early.

Blanking of telemetry refers to a technique in which one ore more components or circuits of telemetry unit 32 are temporarily disabled and/or protected by IMD 10. A blanking period refers to the period of time during which such banking occurs. In accordance with the invention, blanking of telemetry components can be coordinated with the application of MRI electromagnetic radiation bursts in order to ensure that telemetry does not occur during the bursts.

Once the burst interval is done (yes branch of 73), IMD 10 terminates the telemetry blanking period (74). Thus, the telemetry components that were disabled during the blanking interval are reactivated following the blanking period. Accordingly, following termination of the blanking period, IMD 10 is fully capable of telemetric communication. This is very useful because IMD 10 may be capable transmitting sensed information indicative of patient conditions following a burst. Accordingly, blanking telemetry of IMD 10 only at selected times during MRI techniques may provide a number of advantages over a complete disabling of the telemetry of IMD 10 during MRI, most notably that patient conditions can be monitored communicated to programmer 50 during the MRI.

Following termination of the blanking period, the process may repeat if another MRI radiation burst is to be performed (yes branch of 75). Alternatively, the timing information measured or received in a signal from MRI device 20 may define a number of MRI radiation bursts, e.g., a sequence of bursts. In that case, a number of telemetry blanking periods may be executed by IMD 10 in response to one received signal that communicates the sequence to IMD 10. Clock synchronization between IMD 10 and MRI device 20 may further improve telemetric blanking for a sequence of bursts. In that case, information communicated from MRI device 20 to IMD 10 may be used to achieve such clock synchronization.

Figure 5:
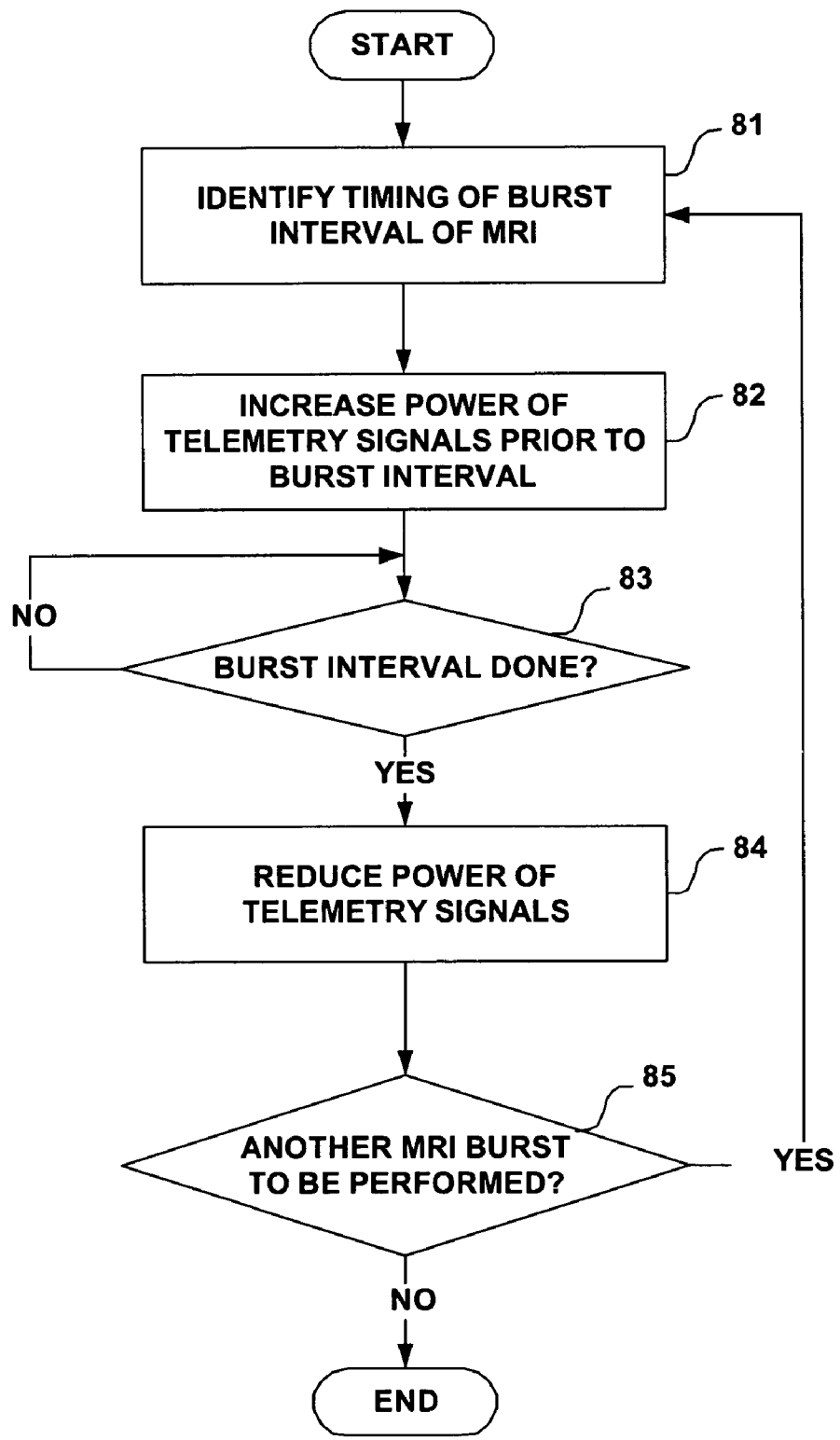

FIG. 5 is another flow diagram illustrating a technique for coordinating telemetry of a medical device with MRI techniques. As shown, IMD 10 identifies timing of a burst interval of MRI (81). Again, IMD 10 may identify such timing by receiving a signal indicative of the timing from MRI device 20 or programmer 50, or by measuring the presence of an electromagnetic radiation burst and calculating the timing. Upon identifying the timing of a burst interval IMD 10 increases the power for its telemetry just prior to the burst interval (72). In particular, IMD control unit 38 may send control signals to telemetry unit 32 to effectuate a telemetric power increase. Advantageously, an increase in power of telemetry signals may allow for communication during the burst interval. Moreover, because MRI is generally performed in a shielded environment, increases in power above governmental regulatory limits may be allowable in some cases.

Once the burst interval is done (yes branch of 83), IMD 10 reduces the power of its telemetry signals back to the original levels (84), e.g., by IMD control unit 38 sending control signals to telemetry unit 32. Then, following termination of the blanking period, the process may repeat if another MRI radiation burst is to be performed (yes branch of 85). Alternatively, the timing information in a received signal may define a number of MRI radiation bursts, e.g., a sequence of bursts. In that case, a number of intervals in which telemetry power is increased during burst intervals may be executed by IMD 10 in response to one received signal that communicates the sequence to IMD 10. Clock synchronization between IMD 10 and MRI device 20 may further improve the coordination of power increases of telemetry with burst intervals. Telemetric power increases during burst intervals may provide advantages similar to the blanking techniques illustrated in FIG. 4, in that telemetry can be effective during the MRI procedure. Moreover, telemetric power increases may provide additional advantages over telemetric blanking techniques such as those illustrated in FIG. 4, in that when power increases are used, telemetry can still be performed during the burst intervals and not just between successive burst intervals.

Figure 6:
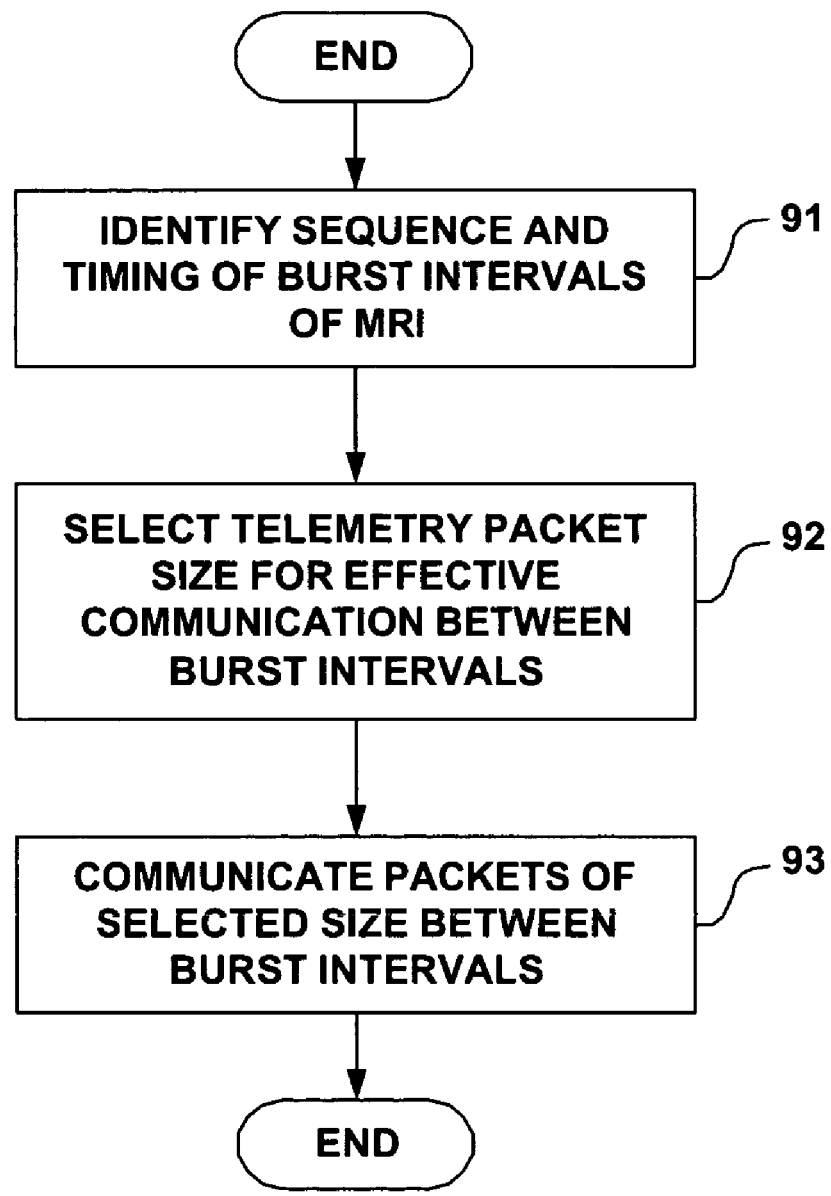

FIG. 6 is another flow diagram illustrating a technique for coordinating telemetry of a medical device with MRI techniques. As shown, IMD 10 identifies a sequence and timing of MRI burst intervals (91). IMD 10 may identify such sequence and timing by receiving a signal indicative of the sequence and timing from MRI device 20 or programmer 50, or by measuring the presence of electromagnetic radiation bursts and calculating the sequence and timing. Upon identifying the sequence and timing of a burst interval, IMD 10 selects a packet size for telemetry (92). In particular, IMD control unit 38 may select the packet size and send control signals to telemetry unit 32 to effectuate transmission of packets according to the selected size. The selected size may be small enough to ensure that one or more packets can be communicated between burst intervals. Accordingly, IMD 10 can subsequently communicate the one or more packets via telemetry during the periods of time between successive burst intervals (93). Adjusting telemetry packet size for coordination with MRI may achieve advantages, in that the telemetry may be effectively used during the MRI.

In some cases, adjustments to packet sizes may be used in concert with other techniques described herein, such as blanking of telemetry during the bursts. In that case, IMD 10 may identify information indicative of a sequence and timing of electromagnetic radiation bursts, define packet sizes for communication between bursts, enter telemetric blanking periods during the bursts, and communicate packets of the selected size between bursts.

Moreover, in accordance with the invention, a number of other modifications or adjustments could be made to telemetry based on identified information associated with the MRI. For example, a specific telemetry mode could be selected for use between burst intervals, or specific use during the MRI. In particular, the use of sound waves or other non-electromagnetic techniques for telemetry, rather than the use of electromagnetic signals may be desirable for telemetry during the MRI, but less desirable when MRI is not being performed. Accordingly, a non-electromagnetic telemetry technique may be selected when MRI radiation bursts are detected or identified. These and other modifications or adjustments could be made to telemetry based on identified information associated with the MRI. In some cases, telemetry may be blanked or adjusted during application of MRI gradient fields, in addition to application of radiation bursts.

A number of embodiments of the invention have been described. However, one skilled in the art will appreciate that the invention can be practiced with embodiments other than those disclosed. The disclosed embodiments are presented for purposes of illustration and not limitation, and the invention is limited only by the claims that follow.

What is claimed is:

1. A method for use in a medical device for controlling wireless telemetry during a magnetic resonance imaging (MRI) procedure, the method comprising:
   determining a plurality of time intervals defining a plurality of MRI electromagnetic bursts;
   transmitting wireless telemetry from the medical device during delivery of the plurality of MRI electromagnetic bursts; and
   automatically adjusting the telemetry transmission during the MRI burst delivery in response to the determined plurality of time intervals.

2. The method of claim 1 wherein determining the plurality of time intervals comprises receiving the time intervals from an MRI device.

3. The method of claim 1 wherein determining the plurality of time intervals comprises detecting the MRI bursts and measuring the time intervals.

4. The method of claim 1 wherein the plurality of time intervals comprises a duration of at least one of the plurality of MRI electromagnetic bursts.

5. The method of claim 4 wherein adjusting telemetry comprises blanking a telemetry component in the medical device during the duration.

6. The method of claim 4 wherein adjusting telemetry comprises increasing a power of the telemetry signals transmitted during the duration.

7. The method of claim 4 wherein adjusting telemetry comprises selecting a non-electromagnetic telemetry signal for transmission during delivery of the plurality of MRI electromagnetic bursts.

8. The method of claim 1 wherein the plurality of time intervals comprises an interval between successive MRI bursts.

9. The method of claim 8 wherein adjusting telemetry comprises selecting a data packet size that can be transmitted during the interval between successive MRI bursts.

10. The method of claim 2 further comprising synchronizing a clock of the medical device with an MRI clock.

11. The method of claim 1 further comprising determining a strength of an MRI electromagnetic burst and adjusting the telemetry transmission comprises adjusting the telemetry transmission in response to the determined strength.

12. A medical device, comprising:
   means for determining a plurality of time intervals defining a plurality of MRI electromagnetic bursts;
   a telemetry unit for transmitting wireless telemetry from the medical device during delivery of the plurality of MRI electromagnetic bursts; and
   a control unit configured to automatically adjust the telemetry transmission during the MRI burst delivery in response to the determined plurality of time intervals.

13. The device of claim 12 wherein the means for determining the plurality of time intervals comprises means for receiving the time intervals from an MRI device.

14. The device of claim 12 wherein the means for determining the plurality of time intervals comprises means for detecting the MRI bursts and means for measuring the time intervals.

15. The device of claim 12 wherein the plurality of time intervals comprises a duration of at least one of the plurality of MRI electromagnetic bursts.

16. The device of claim 15 wherein the control unit is configured to blank a telemetry component in the telemetry unit during the duration.

17. The device of claim 15 wherein the control unit is configured to increase a power of the telemetry signals transmitted during the duration.

18. The device of claim 15 wherein the control unit is configured to select a non-electromagnetic telemetry signal for transmission during delivery of the plurality of MRI electromagnetic bursts.

19. The device of claim 12 wherein the plurality of time intervals comprises an interval between successive MRI bursts.

20. The device of claim 19 wherein the control unit is configured to select a data packet size that can be transmitted during the interval between successive MRI bursts.

21. The device of claim 13 further comprising a clock and means for synchronizing the clock with an MRI clock.

22. The device of claim 12 further comprising means for determining a strength of an MRI electromagnetic burst, wherein the control unit is configured to adjust the telemetry transmission in response to the determined strength.

23. The device of claim 12 further comprising means for determining a magnetic gradient, wherein the control unit is configured to adjust the telemetry transmission in response to the determined gradient.

* * * * *

UNITED STATES PATENT AND TRADEMARK OFFICE
CERTIFICATE OF CORRECTION

PATENT NO. : 7,623,930 B2 Page 1 of 1
APPLICATION NO. : 10/673934
DATED : November 24, 2009
INVENTOR(S) : Zeijlemaker et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 984 days.

Signed and Sealed this

Twenty-sixth Day of October, 2010

David J. Kappos
*Director of the United States Patent and Trademark Office*